(12) United States Patent
Allison et al.

(10) Patent No.: US 7,256,325 B1
(45) Date of Patent: Aug. 14, 2007

(54) METHODS FOR TRANSFORMING PLANTS

(75) Inventors: Richard F. Allison, Leslie, MI (US); Jeanne Ohrnberger, Whitemore Lake, MI (US); Rafaz Hoque, New York, NY (US); Mark Desrosiers, Lexington, KY (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/206,852

(22) Filed: Dec. 8, 1998

(51) Int. Cl.
 C12N 15/82 (2006.01)
 C12N 15/84 (2006.01)
 C12N 15/87 (2006.01)
 A01H 1/00 (2006.01)
 C12N 15/29 (2006.01)
 C12N 15/53 (2006.01)

(52) U.S. Cl. .................. 800/292; 800/260; 800/278; 800/294; 800/312; 800/313; 435/189; 536/23.2; 536/23.6

(58) Field of Classification Search ............ 800/278, 800/294, 312; 435/468, 469
See application file for complete search history.

(56) References Cited

U.S. PATENT DOCUMENTS 5,866,778 A * 2/1999 Hartman et al. ............ 800/279
6,166,291 A * 12/2000 Bidney et al. .............. 800/279

OTHER PUBLICATIONS

Songstad et al., Advances in alternative DNA delivery techniques, Plant Cell, Tissue and Organ Culture 40:1-15, 1995.*
An, G., "Binary Ti Plasmid Vectors," Agrobacterium Protocols in Method in Molecular Biology, vol. 44 (Garland, K.M.A. and Davey, M.R. eds.) Humana Press, Totowa, NJ, p. 47-58, 1995.*
Ahokas, H., Transfection of germinating barley seed electrophoretically with exogenous DNA, Theor Appl. Genet. 77:469-472,1989.*
Burchi et al., In vivo electrotransfection: transient GUS expression in ornamentals, Journal of Genetics & Breeding, vol. 49, No. 2, pp. 163-167, 1995.*
Burchi et al., J. Genet. & Breed. 49:163-168(1995).*
Griesbach, et al, An Improved Method For Transforming Plants Through Electrophoresis. Plant Science vol 102, Issue 1, 1994, pp. 81-89.*
Vik, et al, 2001. Stable Transformation Of Pionsettia Via Electrophoresis. Acta Hort. (ISHS) 560:101-103 http://www.actahort.org/books/560/560_12.htm.*
Burchi et al In Vivo electrotransfection: transient GUS expression in ornamentals. J. Genet. and Breed, 49:163-168.*
Zupan et al. The Plant Journal 23(1): 11-28 (2000).*
Zupan et al. Plant Physiology 107: 1041-1047 (1995).*
Gelvin, S. Annual Review of Plant Physiology and Plant Molecular Biology 51: 23-256 (2000).*
Ahokas, H., "Transfection Of Germinating Barley Seed Electrophoretically With Exogenous DNA," Theor. Appl. Genet. 77:469-472 (1989).
An, G., "Binary Ti Plasmid Vectors," Agrobacterium Protocols in Method in Molecular Biology, vol. 44 (Garland) K.M.A. & Davey, M.R. eds.) Humana Press Totowa NJ p. 47-58 (1995).
Griesbach, R.J. et al., "Incorporation Of The Gus Gene Into Orchids Through Embryo Electrophoresis,"0 Acta. Hort. 336:165-169 (1993).
Morikawa, H. et al., "Gene Transfer Into Intact Plant Cells By Electroinjection Trough Cell Walls And Membranes," Gene 41:121-124 (1986).
Murry, L.E. et al., "IV.3 Transformation In Maize Using Low Voltage Electric Current," Biotechnology in Agriculture and Forestry 25:253-261 (1994).
Songstad, D.D. et al., "Advances In Alternative DNA Delivery Techniques," Plant Cell Tissue and Organ Culture 40:1-15 (1995).
Van Wert, S.L. et al., "Electrofusion and Electroporation of Plants," Plant Physiol. 99:356-367 (1992).

* cited by examiner

Primary Examiner—David T. Fox

(57) ABSTRACT

Methods for the transformation of plants are provided. The methods of the present invention comprise the steps of a) contacting the meristematic tissue of a plant and an area of the plant below the contacted meristematic tissue to a power source, wherein the area below the meristematic tissue is contacted to a positive lead and the meristematic tissue is contacted with a DNA-containing medium which in turn is contacted with a negative lead, and b) applying low amperage current, thus causing the DNA to migrate from the DNA-containing medium into the cells of the meristematic tissue. The transformed plants may be grown to maturity. The mature plants may then self-pollinate and the seed from the plant harvested. Both the parent plant, seed from the parent plant, progeny plants and progeny seeds contain the introduced DNA.

12 Claims, 10 Drawing Sheets

| LB | NOS | NPT II |—| 35S | OAO | RB |

FIG. 3

METHODS FOR TRANSFORMING PLANTS

FIELD OF THE INVENTION

The present invention relates generally to methods for transforming plants and more specifically to methods using low amperage current to transform plants.

BACKGROUND OF THE INVENTION

Many economic and scientific interests are tied to the genetic engineering of plants. Several methods of introducing foreign genetic material such as DNA into plants, i.e., transforming plants, have evolved and are currently in use. The most common are *Agrobacterium*-mediated gene delivery, microprojectile bombardment and free DNA delivery to protoplasts.

DNA delivery procedures via *Agrobacterium*, microprojectile bombardment and direct uptake into protoplasts systems require that the transgene be under control of promoter and transcription termination signals that function in plants. The transgene sequence(s) must conform to plant consensus codon usage. Both microprojectile bombardment and protoplast systems (collectively referred to as direct DNA delivery procedures) most commonly introduce transgene sequences carried on high copy number *E. coli* plasmids which are easy to produce in large amounts. *Agrobacterium*-based DNA delivery requires that the transgene of interest be inserted into the T-DNA between the right and left border sequences on either disarmed Ti or Ri plasmids, or binary vectors followed by reintroduction into the appropriate *Agrobacterium* strain.

*Agrobacterium*-mediated transformation is currently the most widely used commercial technique. It requires the production of recombinant *Agrobactrium* containing the gene of interest. Transformation is then achieved by co-cultivation of the recombinant *Agrobactrium* with the mesophyll cells of leaf disks. The leaf disk is routinely used for dicots such as tobacco, soybean and cotton, but has not been found to be effective with monocots. Songstad, D. D. et al., *Plant Cell Tissue and Organ Culture* 40:1-15 (1995).

Although widely used, there are a number of drawbacks to the *Agrobacterium* method. It is time consuming, requiring the production and isolation of a recombinant *Agrobacterium*, a two day co-cultivation period, and regeneration of a plant from a single cultured cell. The method also requires the use of leaf disks which are prepared by enzymatic digestion of plant cells to break down the cell wall. After transformation, a single, transformed cell is selected and grown on antibiotic-containing media to form the new plant. The whole procedure must be carried out using sterile procedures and facilities. In addition, the method involves prolonged tissue culture and requires the capability to regenerate the cultured cells to whole plants.

Transformation of both monocots and dicots can be achieved by particle bombardment. The DNA to be delivered is attached to microparticles such as gold or tungsten beads. The beads are then "shot" into cells using a gun, usually powered by compressed air. This method has been used to transform monocots such as corn, wheat and rice that were shown to be unresponsive to *Agrobacterium*-mediated transformation. Songstad, D. D. et al., *Plant Cell Tissue and Organ culture* 40:1-15 (1995). Particle bombardment however, shares many of the same drawbacks as the *Agrobacterium* method. For example, the entire procedure must be carried out under sterile conditions and individual cells, not seedlings, are transformed. An additional drawback is the expense of the equipment necessary to deliver the DNA-coated microparticles to the cell (e.g., a "gene gun").

Protoplast-mediated transformation is an alternative method for producing recombinant monocot and dicot plants. As with *Agrobacterium*-mediated transformation, cultured mesophyll protoplasts are transformed by introducing foreign DNA. However in protoplast-mediated transformation, the DNA is introduced directly into the cell. Direct delivery of the DNA is achieved by either chemical treatment of the protoplasts to make the cell membranes porous to the DNA or by electroporation. Songstad, D. D. et al., *Plant Cell Tissue and Organ Culture* 40:1-15 (1995); Morikawa, H. et al., *Gene.* 41:121-124 (1986). This method however, shares the drawbacks set forth above for the other methods. In addition, if electroporation is used for DNA delivery, the resulting transformed plants are often sterile.

Recent advances in plant transformation have led to the use of an electrophoretic method for the transformation of plant embryos. The embryos are either removed from the seed, or the seed is dehusked prior to electrophoresis. A cathode is then placed in direct contact with the embryo or seed and a DNA-containing medium is placed between the anode and the embryo or seed. Application of current causes the DNA to migrate from the medium into the embryo or seed cells. The embryos or seeds are then germinated. Barley and corn embryos as well as orchid protocorms have been transformed by this method. Ahokas, H., *Theor. Appl. Genet.* 77:469-472 (1989); Murry, L. E. et al., *Biotechnology in Agriculture and Forestry* 25:253-261 (1994); Griesbach, R. J. et al., *Acta. Hort.* 336:165-169 (1993). An advantage of this method is that it does not require sterile conditions. However, barley embryos transformed by this method produced sterile plants. Ahokas, H., *Theor. Appl. Genet.* 77:469-472 (1989). The method is also time-consuming, wherein the embryos must either be removed from the seeds or the seeds must be treated, i.e. dehusked, before transformation. This method also requires large amounts of plasmid DNA (approximately 10 μg). Moreover, most zygotic embryos are sensitive to the amount of current applied and often will not germinate after treatment.

It would thus be desirable to provide an improved method for transforming plants. It would be desirable for the improved method to be applicable in both dicots and monocots. It would also be desirable to provide a method for transforming plants that may be performed under normal (i.e., non-sterile) conditions with little or no preparation of the plant material. It would further be desirable to provide a method for transforming plants that produces non-sterile transformants, so that the progeny of the transformed plants also carry the transgene. It would also be desirable to provide a method for transforming plants that is commercially attractive, e.g., allowing transformation of a large number of plants at one time with high yields. It would further be desirable to provide a method for transforming plants wherein basic materials and equipment are employed so that the method is cost-effective.

SUMMARY

Methods for the transformation of plants are provided. The methods of the present invention comprise the steps of a) contacting the meristematic tissue of a plant and an area of the plant below the contacted meristematic tissue to a power source, wherein the area below the meristematic tissue is contacted to a positive lead and the meristematic tissue is contacted with a DNA-containing medium which in turn is contacted with a negative lead, and b) applying low amperage current, thus causing the DNA to migrate from the DNA-containing medium into the cells of the meristematic tissue. The transformed plants may be grown to maturity. The mature plants may then self-pollinate and the seed from the plant harvested. Both the parent plant, seed from the parent plant, progeny plants and progeny seeds contain the introduced DNA.

Additional objects, advantages, and features of the present invention will become apparent from the following description, taken in conjunction with the accompanying drawings and claims.

BRIEF DESCRIPTION OF THE DRAWINGS

The various advantages of the present invention will become apparent to one skilled in the art by reading the following specification and subjoined claims and by referencing the following drawings in which:

FIG. 3 is a schematic showing sequence insertion of the nptII reporter transgene and OAO transgene;

DETAILED DESCRIPTION OF THE PREFERRED EMBODIMENTS

Figure 1:
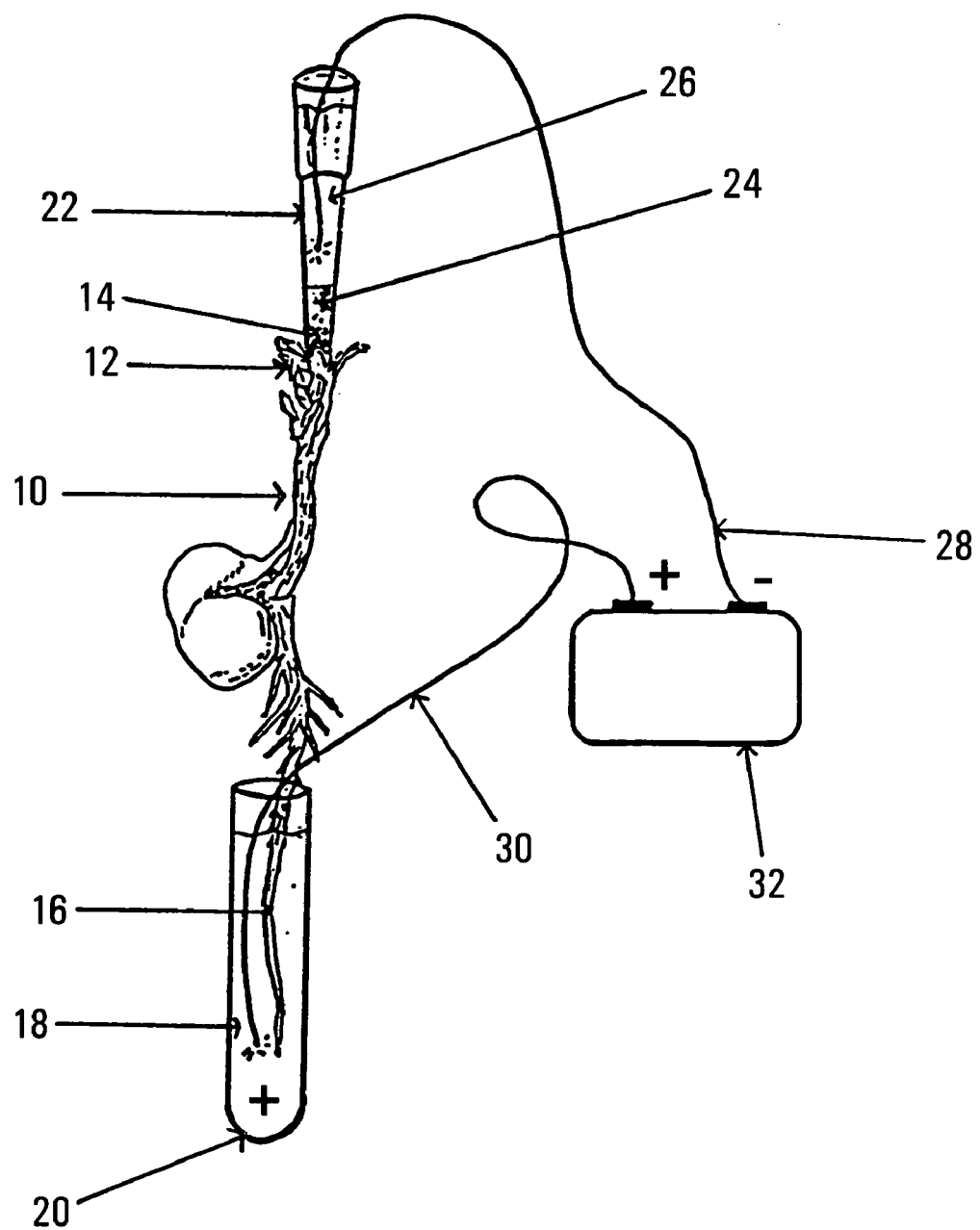
FIG. 1 is a schematic representation of one embodiment of the transformation methods of the present invention.

Methods for plant transformation are provided. The methods of the present invention comprise the steps of a) contacting meristematic tissue of a plant and an area of the plant below the contacted meristematic tissue to a power source, wherein the area below the contacted meristematic tissue is contacted with a positive lead and the meristematic tissue is contacted with a DNA-containing medium which in turn is contacted with a negative lead of the power source, and b) applying low amperage current, causing the DNA to migrate from the DNA-containing medium into the cells of the meristematic tissue. The positive electrode may be positioned anywhere in contact with the plant below the meristematic tissue to be transfected, that will facilitate the flow of electrical current through the meristematic tissue. Suitable areas of the plant to be contacted with the positive electrode include, without limitation, the stem and roots of the plants. The transformed plants are then grown to maturity and the mature plants may self-pollinate. Both the parent plant, seed from the parent plant and progeny plants and progeny seeds contain the introduced DNA.

In one embodiment, a method of the present invention targets transformation of actively dividing cells in the apical meristem of a plant seedling which contains cells that will eventually undergo meiosis in the reproductive flower parts and lead to embryo development, allowing the transgene to be passed on to successive generations. In another embodiment, a method of the present invention targets cells in the developing lateral meristem of a plant. Lateral meristems may be encouraged to develop by removing the apical meristem.

It will be appreciated that the desired traits of the transformed plant will determine the transgene to be introduced into the plant. It will further be appreciated that although DNA is described herein in detail as the "transgene" or genetic material that is transferred to the plant cells, any suitable genetic material may be employed including cDNA, genomic or newly synthesized DNA, including DNA that is isolated from a plasmid or other natural source. The term "transgene" therefore includes any genetic material that is transferred to the plant cells. It will also be appreciated that the term "plant" includes both mature plants as well as seedlings.

The methods presented herein can thus be used to produce transgenic plants that are resistant to viral, bacterial and fungal diseases. For example, introduction of the gene encoding barley oxalic acid oxidase to soybeans, may confer resistance to white mold. Transgenes can also be introduced that allow plants to produce new products or biochemicals or to enhance the production of a naturally-produced product or biochemical. For example, the gene encoding acetyl-CoA carboxylase can be introduced into a plant such as soybean, to increase acetyl-CoA carboxylation, thereby increasing the oil production in the plant. Hence, any genetic material that has been introduced into plants using the methods known in the art can also be introduced using the methods of the present invention.

In one embodiment, the transgene to be introduced into a plant by the methods of the present invention is introduced as part of a plasmid vector. The plasmid can be selected from those used in current plant transformation methods. Non-limiting examples are the binary Ti plasmid vectors used for direct DNA transfer and *Agrobacterium*-mediated transformation (An, G., *Agrobacterium* Protocols in Method in Molecular Biology, Vol. 44 (Garlanc) K. M. A. & Davey, M. R. eds.) Humana Press Totowa N.J. p. 47-58 (1995)) and *E. coli* vectors such as pBr322 (Songstad, D. D. et al., *Plant Cell Tissue and Organ Culture* 40:1-15 (1995); Ahokas, H., *Theor. Appl. Genet.* 77:469-472 (1989)). In another embodiment, the plasmid vector containing the transgene can be linearized before transformation. Although transformation will occur using circular plasmid vectors, higher rates of transformation may be achieved using linearized plasmid vectors. The transgene may also be removed from the plasmid completely (the plasmid DNA, required for amplification of the transgene, does not have to be physically connected to the transgene for transformation). It will also be appreciated that any vector system known to those skilled in the art, may be employed in the methods of the present invention.

Any plant, including plant seedlings, may be transformed by the methods of the present invention, including both dicots and monocots. Examples of such plants include, but are not limited to, dry bean, soybean, corn, barley, cucumber and cotton. The plants to be transformed are preferably seedlings, about five to ten days old. Seedlings may be produced by a number of different methods. One method is to place seed in a moist environment at a temperature of about 25-35° C. under 12 hours of fluorescent light per day until the seed germinates. The seed can be placed between sheets of damp paper or cloth such as, but not limited to, filter paper, paper towels or cotton towels. The seeds and cloth are then placed in a container such as a petri dish or a sealed bag in order to retain a moist atmosphere. It will be appreciated that the amount of time necessary for a seed to germinate will depend on the type of seed being germinated and the temperature.

In another embodiment, a seedling is rinsed with deionized water and a collar is placed around the stem just below the cotyledons to allow for placement into a bottom container. The collar can be foam, rubber or any other material that allows placement of the seedling into the container.

FIG. 1 is a schematic representation of one embodiment of the transformation methods of the present invention. A plant seedling (10) has developing leaves (12) that are separated to expose the apical meristem (14). The developing root (16) of the seedling (10) is placed in a first buffer solution (18) in a first container (20). The first container (20) can be any shape and can be made of glass, plastic, or any other non-conductive material that is non-toxic to the seedling. The apical meristem (14) is in contact with DNA-containing medium (24) in a second container (22) that is open on both ends. The second container can also be any shape and can also be made of any non-toxic, non-conductive material such as glass or plastic. In a preferred embodiment, the second container is a yellow pipet tip or a glass tube. A second buffer solution (26) is placed above the DNA-containing medium (24). First and second buffer solutions (18) and (26) are electrophoresis buffers and may be the same solution or different solutions. Any buffer that efficiently conducts electricity and is non-toxic to seedlings may be employed as an electrophoresis buffer, wherein examples of suitable buffers include, without limitation, 10 mM Hepes, 5 mM $MgCl_2$, 0.5% w/v ascorbic acid, 120-140 mM LiCl, pH 7.2; 40 mM Tris-acetate, 2 mM EDTA, pH 8.2; and, 89 mM Tris-phosphate, 2 mM EDTA, pH 8.2. The pH is that which is non-toxic to the plant.

Negative electrode (28) and positive electrode (30) are connected to a power source (32). The negative electrode (28) is placed in the second buffer solution (26) and the positive electrode (30) is placed in the first buffer solution (18). The electrodes can be composed of any material commonly used to conduct electricity such as platinum, silver, chloridated silver or copper wire. A low amperage current is applied, causing the negatively-charged DNA in the DNA-containing medium (24) to migrate away from the negative electrode (28) and towards the positive electrode (30), thereby moving the DNA from the DNA-containing medium (24) into the apical meristem (14). The power source can be any source that produces a low amperage current. The current is that which effectively moves the DNA into the meristem without irreversibly damaging the plant. In one embodiment, the current is in the range of about 0.001 to about 1 mA. The power source can be a commercially available power supply or a simple lantern battery with an attached rheostat to control the amount of current flow.

As described, current is applied to the electrodes (28) and (30), causing transformation of the seedling (10). The negatively-charged DNA will migrate out of the DNA-containing medium (24) away from the negatively-charged electrode (28) and toward the positively-charged electrode (30) and apical meristem (14) of the seedling (10). While not wishing to be bound by theory, it is believed that the electrical charge causes the cell membranes of the meristem cells to become more permeable to the DNA in a manner similar to electroporation or the DNA may be acquired by the plant cells by undetermined natural mechanisms. A low amperage current is used however, rather than a capacitor discharge as in electroporation, to move the DNA into the meristem, while doing as little damage to the plant as possible. The methods of the present invention are thus analogous to an electrophoresis gel in which the negatively-charged DNA migrates through the gel towards the positive electrode.

It should be appreciated that low amperage current will preferably be in the range of about 0.001 to about 1 mA. More preferably, the low amperage current employed in the methods of the present invention will be in the range of about 0.1 to about 0.5 mA. The amount of time that the current is applied is inversely proportional to the amount of current applied. The higher the amount of current, the faster the DNA will migrate into the meristem and therefore, the shorter the amount of time the current need to be applied. Suitable time and current combinations can be estimated by those skilled in the art and may be facilitated by either staining the DNA and monitoring its progress through the plant or adding or layering a dye on top of the DNA-containing medium. The dye will migrate through the DNA-containing medium at about the same rate as the DNA, thereby allowing monitoring of the migration of the DNA. An example of a suitable dye is xylene cyanol FF. It will be appreciated that the dye would most likely not be used during normal transformation as it may be toxic or mutagenic. Optimal values for time and current will depend on the plant species and variety and may be determined by those skilled in the art.

The seedlings may be removed from the apparatus after electrophoretic transformation, soaked in distilled water for about 10 minutes, and planted in appropriate soil for the variety of plant being transformed. The potted seedlings may then be enclosed in a clear chamber, such as a plastic bag, to help retain a moist environment. The contained seedlings may then be placed in ambient light for 24 hours followed by fluorescent light for an additional 24 hours before removing the seedlings from the container. The seedlings may then be assessed for recovery and within 2-4 days removed to a greenhouse. The plants may then be allowed to mature and self-pollinate, and the seeds may be harvested and planted to produce transformed progeny.

Both parent plants and progeny may be analyzed using known techniques for the presence of the introduced DNA. Plant DNA can be analyzed via polymerase chain reaction (PCR) amplification and Southern analysis. Leaf tissue is homogenized to release the DNA which is then used for PCR analysis or Southern analysis. For PCR analysis, the DNA is amplified with primers specific for the DNA of interest, namely the transgene. Controls include untransformed plant tissue and plants transformed with the transforming plasmid lacking the transgene. If the gene of interest is present in the potential transformant, it will appear as an amplified band when the PCR sample is analyzed, typically by agarose gel electrophoresis.

Transformation can also be assessed by analyzing the plants for the presence of the protein encoded by the transgene. Such assessments may be made using standard methods known to those skilled in the art. Non-limiting examples of such methods are ELISA and Western blotting, as well as assaying for protein activity if the transgene encodes an enzyme or the substrate of an enzyme.

The present invention may be better understood in connection with the following example, which is presented for purposes of illustration and not by way of limitation.

SPECIFIC EXAMPLE

Summary

DNA consisting of several marker genes unique to bean tissue was amplified by traditional cloning techniques, purified and concentrated. This DNA was incorporated into a 3 mm agarose plug of approximately 10 µl, in the tip of a small plastic pipette, 220 µl capacity. Buffer filled the remaining portion of the plastic tip above the plug. This tip was placed in contact with the dome of the apical meristem of a bean seedling. The base of the seedling was submerged in a similar buffer and a low amperage direct current (e.g., 0.200 mA) was applied in such a way that the negatively-charged DNA migrated from the agarose tip into the apical meristem. The current was applied for less than 30 minutes after which the seedling was transferred to soil and encouraged to grow. Buffer conditions, DNA concentrations, transformation durations and amperage which avoid damage to the seedlings are controlled as further described herein. Incorporation of the DNA into the chromosomes is thought to be enhanced by inclusion of Agrobacterium T-DNA border sequences that flank the marker genes. The seedlings were allowed to mature, self pollinate and set seed. These seeds were germinated and the progeny plants were evaluated for the presence of the marker gene, in this case NPTII.

Materials and Methods

Figure 2:
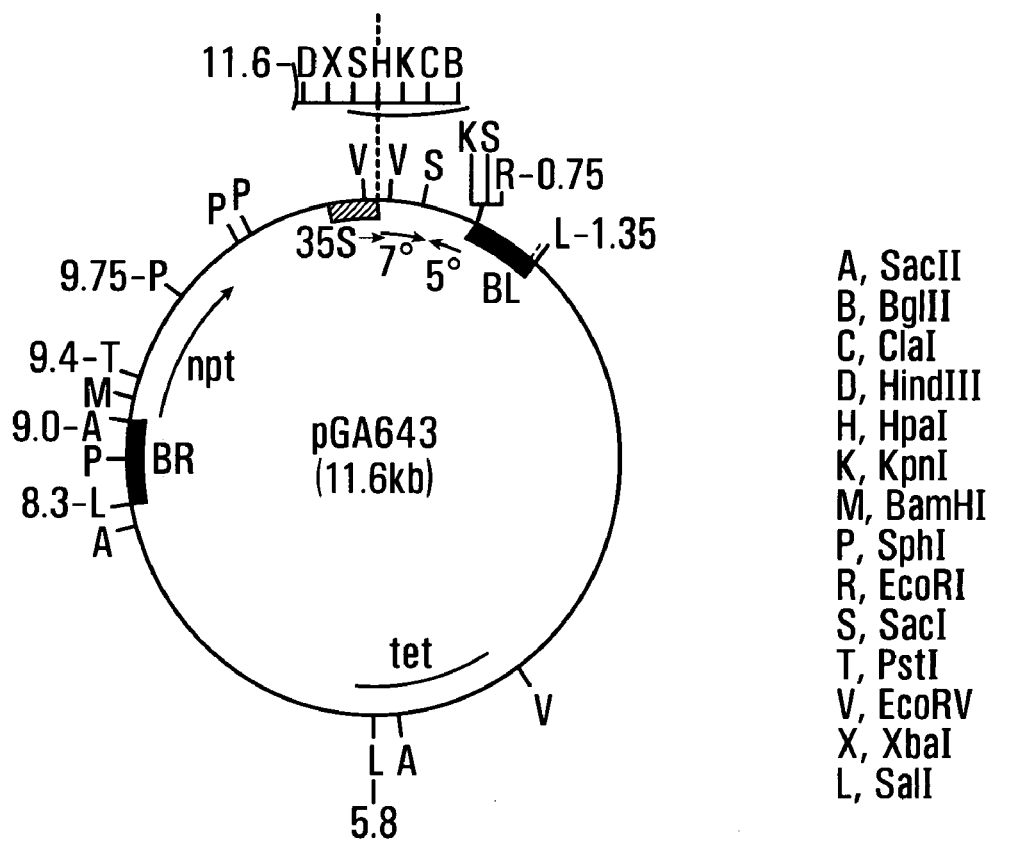
FIG. 2 is a schematic of the pGA643 plasmid map.
Figure 3:
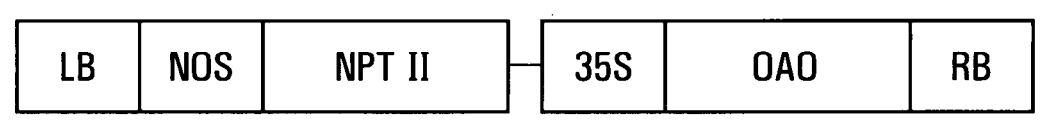

Plasmid preparation. Plasmid pJOG-1 was prepared by inserting the gene for barley oxalic acid oxidase (OAO) and the reporter gene nptII, into pGA643 (An, G., *Agrobacterium* Protocols in Method in Molecular Biology, Vol. 44 (Garlanc) K. M. A. & Davey, M. R. eds. Humana Press Totowa, N.J. p. 47-58 (1995)) isolated from a cesium chloride gradient. pGA643 (FIG. 2) was originally designed to be used with *Agrobacterium*-mediated transformation and was selected because it has the left and right border sequences which facilitate integration in the Agro system. FIG. 3 shows the OAO insert. The border sequences are the proposed active sites for DNA integration into the chromosome. While the 35S transcriptional promoter was used in this construct, the transformation process is not dependent on this promoter or any other specific transcription promoter. Thus, any transcription promoter active in plants will work to drive the expression of the inserted gene. In FIG. 3, LB plasmid (Agro)), NOS represents the transcriptional promoter sequence for gene expression (from Agro), NPTII represents antibiotic resistance marker gene, 35S represents the transcriptional promoter for gene expression (from Cauliflower Mosaic Virus), OAO represents the oxalic acid oxidase gene (from barley), and RB represents right border insertion sequence (from Agro). For transformation, the plasmid was cut with the restriction enzyme Sal I which linearized the plasmid just beyond the right and left *Agrobacterium* Ti border sequences. The digest was performed so the final concentration of pJOG-1 was 1-2 ug/ul.

Soybean varieties. For the oxalic acid oxidase transformation, soybean varieties Corsoy 79, Olympus and Novartis 19-90 were used. Transformation was also performed on dry bean varieties Aztec, Mackinac, and Kodiak.

Transformation buffers
Buffer 1 (reservoir buffer)
10 mM Hepes
5 mM $MgCl_2$
0.5% w/v Ascorbic Acid
120 mM LiCl
pH 7.2
Buffer 2 (tip buffer)
10 mM Hepes
5 mM $MgCl_2$
0.5% w/v Ascorbic Acid
140 mM LiCl
pH 7.2

Transformation of soybeans and dry beans. A preferred embodiment has a multimeter connected to a 45-Volt battery pack, which is capable of producing 1 mA of current. Positive and negative leads that have a copper grasping clamp are used to deliver current from the multimeter. In line to the multimeter is a rheostat that controls the current.

The electrodes utilized in the transformation process are chloridated silver wire and platinum. The chloridation is completed by submerging the silver wire attached to the positive lead in a dilute hydrochloric acid solution and maintaining a current of 0.500 mA for 15 min. The platinum is maintained to be clean and free from debris.

The negative lead is attached to the silver wire for the transformation process. The positive lead is attached to the platinum electrode. The holding apparatus for the transformation is a modified 50-mL tube. The bottom of the tube is cut off. The cap is secured to the tube and sealed with silicone sealant. A slit is cut in the side of the tube and the platinum electrode is inserted and the remaining gap is sealed with silicone sealant. For transformation, this tube is used as a reservoir for transformation buffer number 1.

Plant seeds are germinated in petri dishes with layers of filter papers soaked with distilled water under fluorescent lighting for a 12 hour photoperiod. A seedling between five to ten days old (depending on the plant species and variety) is rinsed with distilled water and is supported within the holding tube by a foam collar placed just below the cotyledons. The roots of the seedling and foam plug are secured in the top of the modified tube (FIG. 1). The cotyledon and leaf primordia of the seedling are separated to expose the apical meristematic dome.

The apical meristem is contacted by a yellow tip. The yellow tip has approximately 15 ul of a mixture of 0.8% agarose in buffer number 2 and 1-2 ug DNA, with transformation buffer number 2 overlaid on top. The chloridated silver electrode is placed in transformation buffer number 2. The yellow tip is brought in contact with the apical meristem of the seedling (FIG. 1). Completion of the circuit is maintained so long as the yellow tip is in contact with the apical meristem.

The current is maintained for 30 minutes in a range of 0.100 mA to 0.500 mA, however optimal values vary depending on the plant species and variety. Following the 30-minute transformation process, the seedling is removed from the apparatus and soaked in distilled water for 10 minutes prior to planting in appropriate soil. The pot and seedling are then enclosed in a plastic bag for 24 hours in ambient light. Bagged plants are then placed under fluorescent light arrays for another 24 hours before removing the bags. Following bag removal, plants are assessed for survival and within 2-4 days removed to the transgenic greenhouse.

Analysis of plant tissue. Seed from the initially transformed plant is grown in transgenic greenhouses. The first trifoliate leaf is sampled with ELISA using the 5'-3' nptII ELISA kit. Assays were handled per manufacturer instructions. The ELISA assay uses an antibody to detect the neomycin phosphotransferase protein (nptII). The assay can detect picogram amounts of the protein. The assay is read utilizing a horseradish peroxidase color assay, which is read with a spectrophotometer at 405 nm. Negative controls are untransformed plant tissue. Positive controls are Arabidopsis plants transformed via *Agrobacterium*.

Plant DNA is also analyzed via polymerase chain reaction (PCR) and Southern analysis. Leaf tissue is homogenized to release the DNA. The DNA is then used in PCR with primers specific for nptII or for the transgene, in this case, oxalic acid. Negative controls are untransformed plant tissue. Positive controls are the transforming plasmid.

Southern analysis digested 5-10 μg DNA with restriction enzyme Nco I. DNA was electrophoresed on 0.8% agarose gels and stained with ethidium bromide for visualization. Standard techniques were employed to nick and hydrolyze the DNA in the gel prior to transfer to Magna-charge nylon membrane. DNA was cross-linked to the membrane by vacuum baking at 80° C. for two hours. Band isolated JOG-1 was random hexamer labeled with $^{32}$P. Hybridization of the probe to the membrane was carried out at 65° C. overnight. Probe was removed with high stringency washes with 0.1× SSC, 0.1% SDS. Washed membranes were exposed to x-ray film for 2-7 days, depending on probe signal.

Oxalic acid oxidase activity in leaf homogenates was determined spectrophotometrically. Leaf discs about 1 cm in diameter (about 1-2 punch), 1 BB, and 400 μl of 0.1M succinate buffer, pH 3.5 were added to a tube. The leaf discs were then homogenized automatically using a Brinhman Polytron 20,000 rpm for 30 seconds. The resulting homogenate was centrifuged at 4,000 rpm for 20 minutes and the supernatant removed by carefully decanting. The pellet was resuspended in 400 μl of 0.1M succinate buffer, pH 3.5, mixing well. After centifugation, the supernatant was again removed by decanting. The pellet was resuspended in 400 μl of 0.1 M succinate buffer, pH 3.5 and 50 μl of 10 mM oxalate, pH. 3.5 and incubated at 37° C. for 2 hr with constant shaking. The sample was then centrifuged at 4,000 rpm for 20 minutes and 100 μl aliquots of the supernatant transferred to the wells of microtiter plate. To the supernatant in the microtiter plate, 17.5 μl 0.2 M Tris-HCl, pH 7.0 and 82.5 μl developing solution (8 mg 4-amino antipyrine, 400 μl peroxide and 20 μl N,N-dimethylanaline in 100 ml 0.2 M Tris-HCl, pH. 7.0) were added and mixed well. The absorbance of the resulting solution was determined at 550 nm.

Results

The original transformed plants ($T_o$) were grown to maturity, self-pollinated, and the seeds collected. These seeds were germinated and grown and the process repeated to produce $T_1$, $T_2$, $T_3$ and $T_4$ progeny. Various tests were used to establish that the transgenes were stably introduced to the plant DNA and inherited by the resulting progeny.

Figure 4:
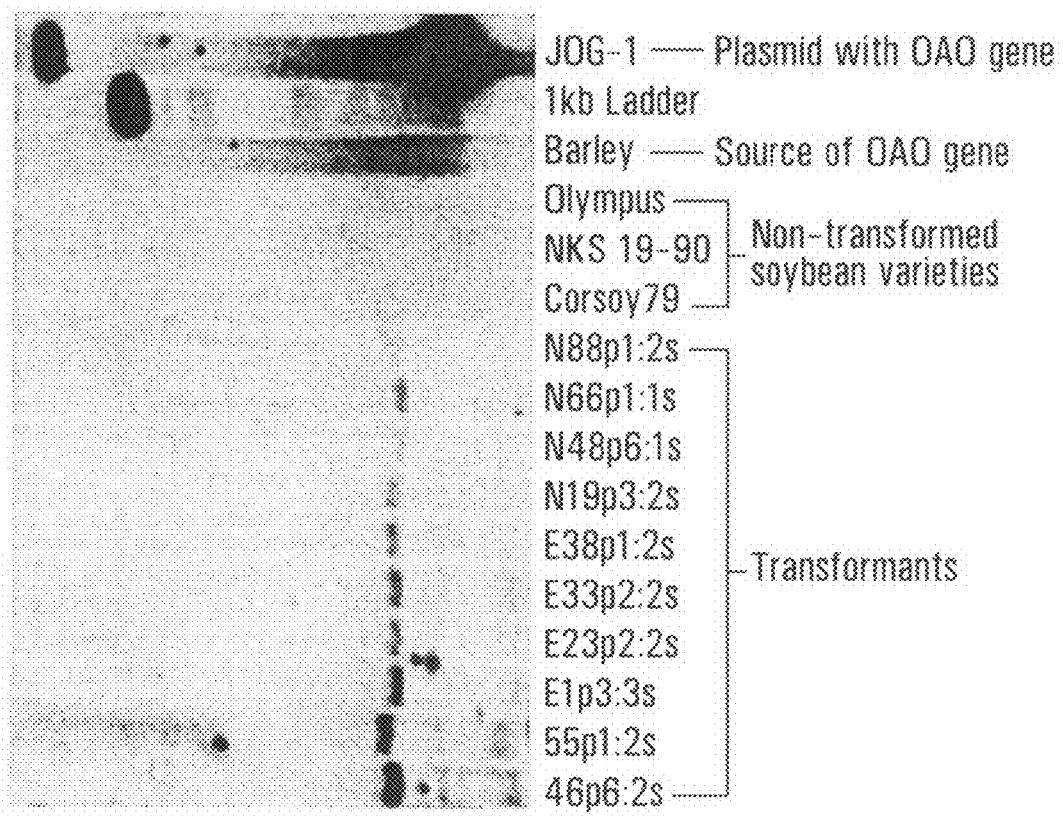
FIG. 4 is a photograph of a Southern blot showing the presence of the barley OAO transgene in the $T_1$ progeny of the original transformed plant.

Southern blot analysis of several soybean varieties show transformation of the progeny seedlings using the methods of the present invention. Olympus, Corsoy 79 and Novartis 19-90 varieties of soybean were transformed using plasmid JOG-1 containing the barley OAO gene. Southern blot analysis of the $T_1$ progeny of these plants shows the presence of the barley OAO gene (FIG. 4, lanes N88p1:2s through 46p6:2s) but not in non-transformed controls (FIG. 4, lanes Olympus, NKS 19-90 and Corsoy 79).

Figure 10:
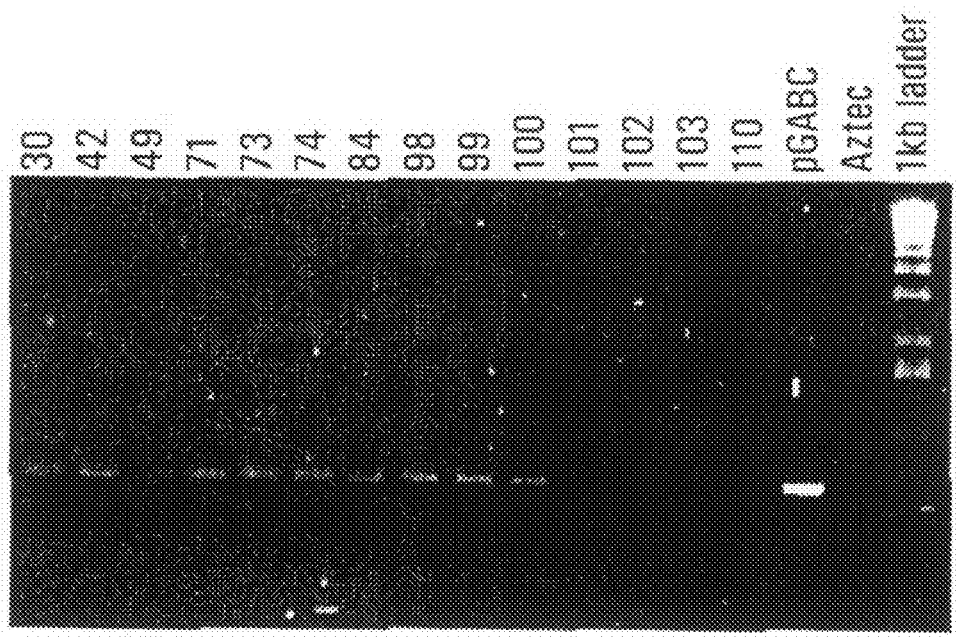
FIG. 10 is a photograph of an agarose gel showing the presence of nptII transgene after PCR amplification in the originally transformed Aztec dry bean seedlings.

The Aztec variety of dry bean was also successfully transformed using plasmid JOG-1. PCR amplification of the reporter gene, nptII, from the progeny of the originally transformed plants showed the reporter gene in 10 out of 14 plants (FIG. 10).

Figure 8:
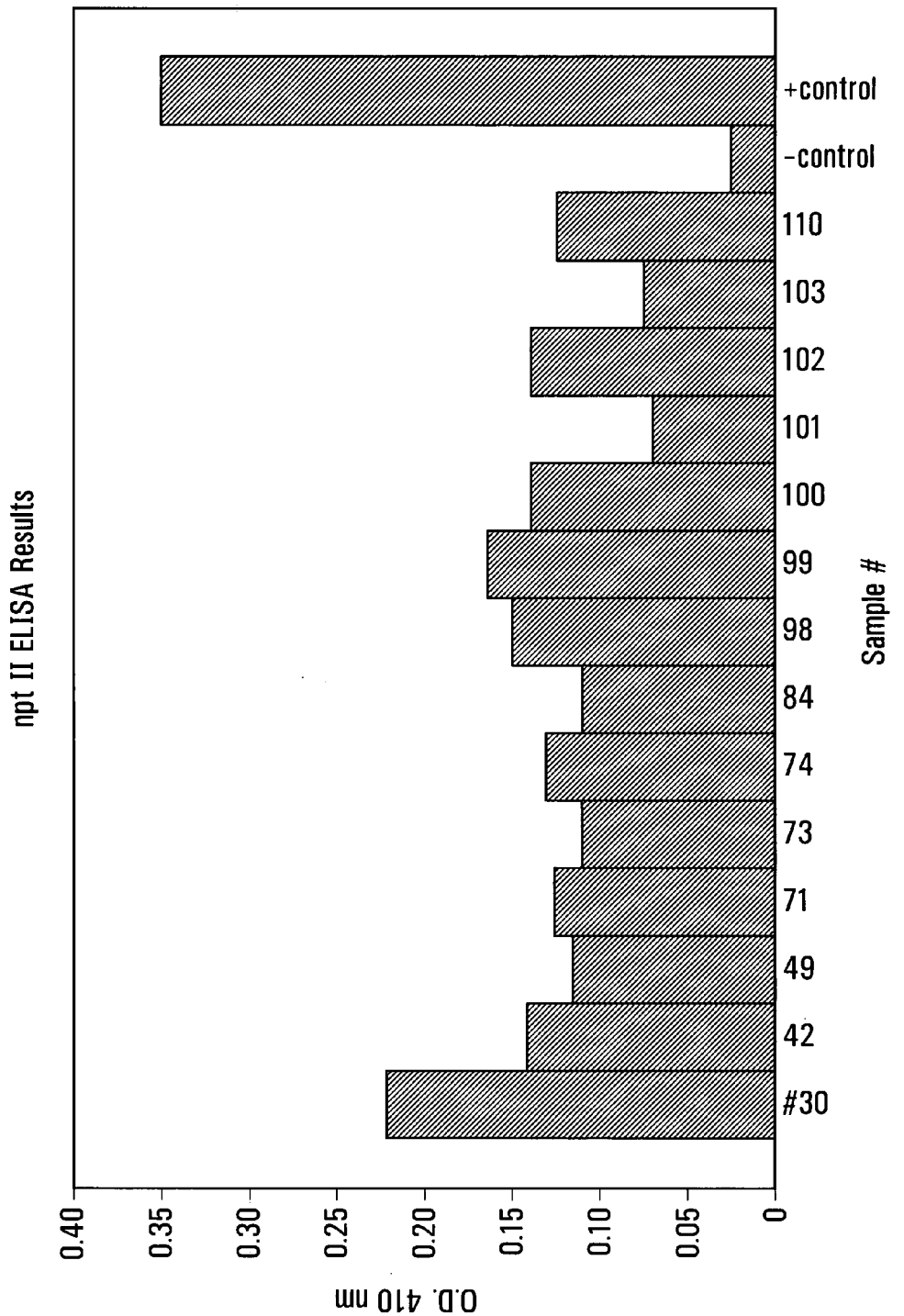
FIG. 8 is a graph showing the expression of NPTII protein in the $T_1$ progeny of the originally transformed Aztec dry bean seedlings as determined by ELISA.
Figure 9:
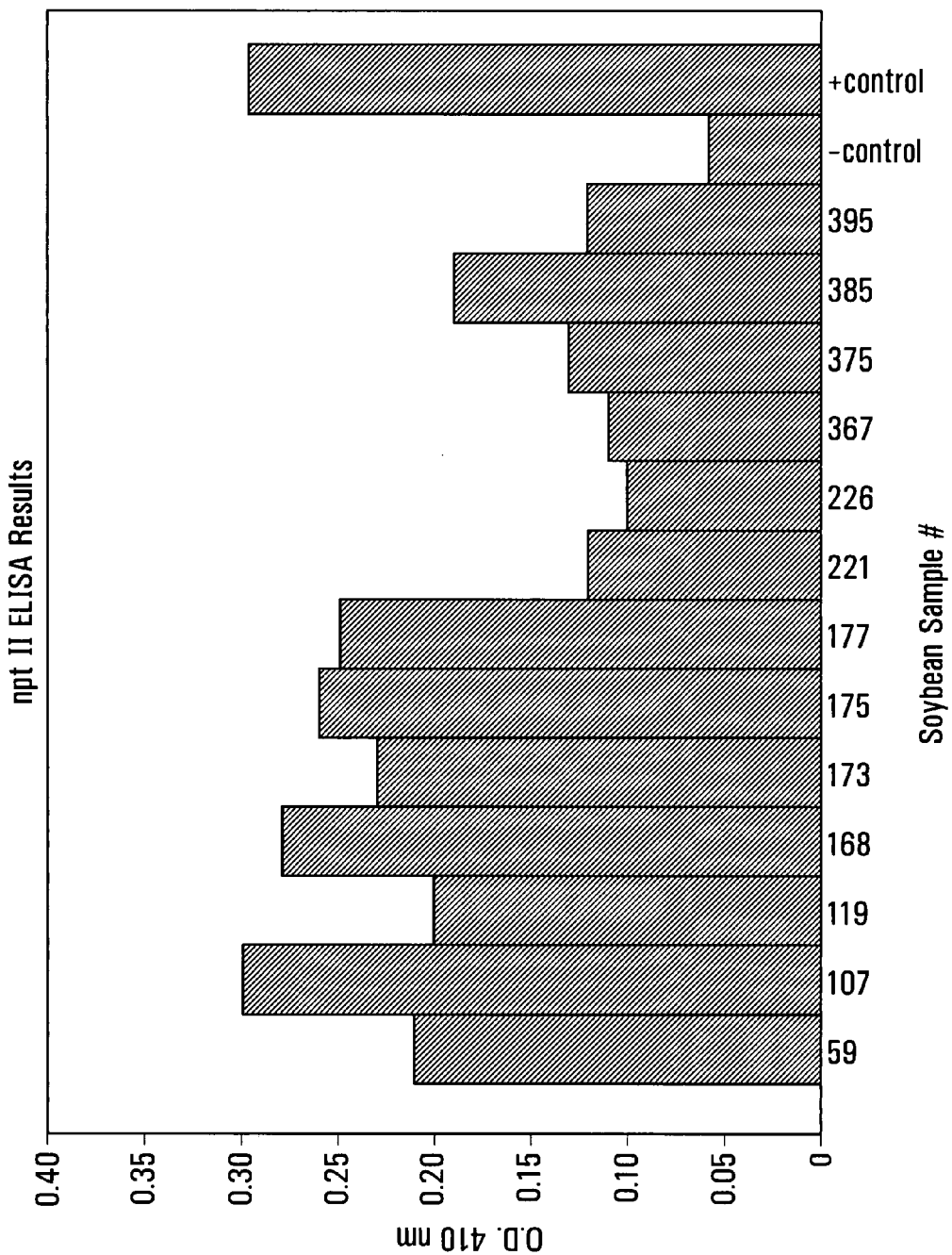
FIG. 9 is a graph showing the expression of NPTII protein the $T_1$ progeny of the originally transformed Corsoy 79 soybean seedlings as determined by ELISA.

The OAO gene, as determined by various assays, was present in all subsequent progeny. The $T_1$ generation of originally transformed Corsoy 79 soybean and Aztec dry bean plants were analyzed for the presence of NPTII protein by ELISA. The data in FIGS. 8 and 9 show a significant amount of NPTII present in the progeny of both soybean and dry bean.

Figure 5:
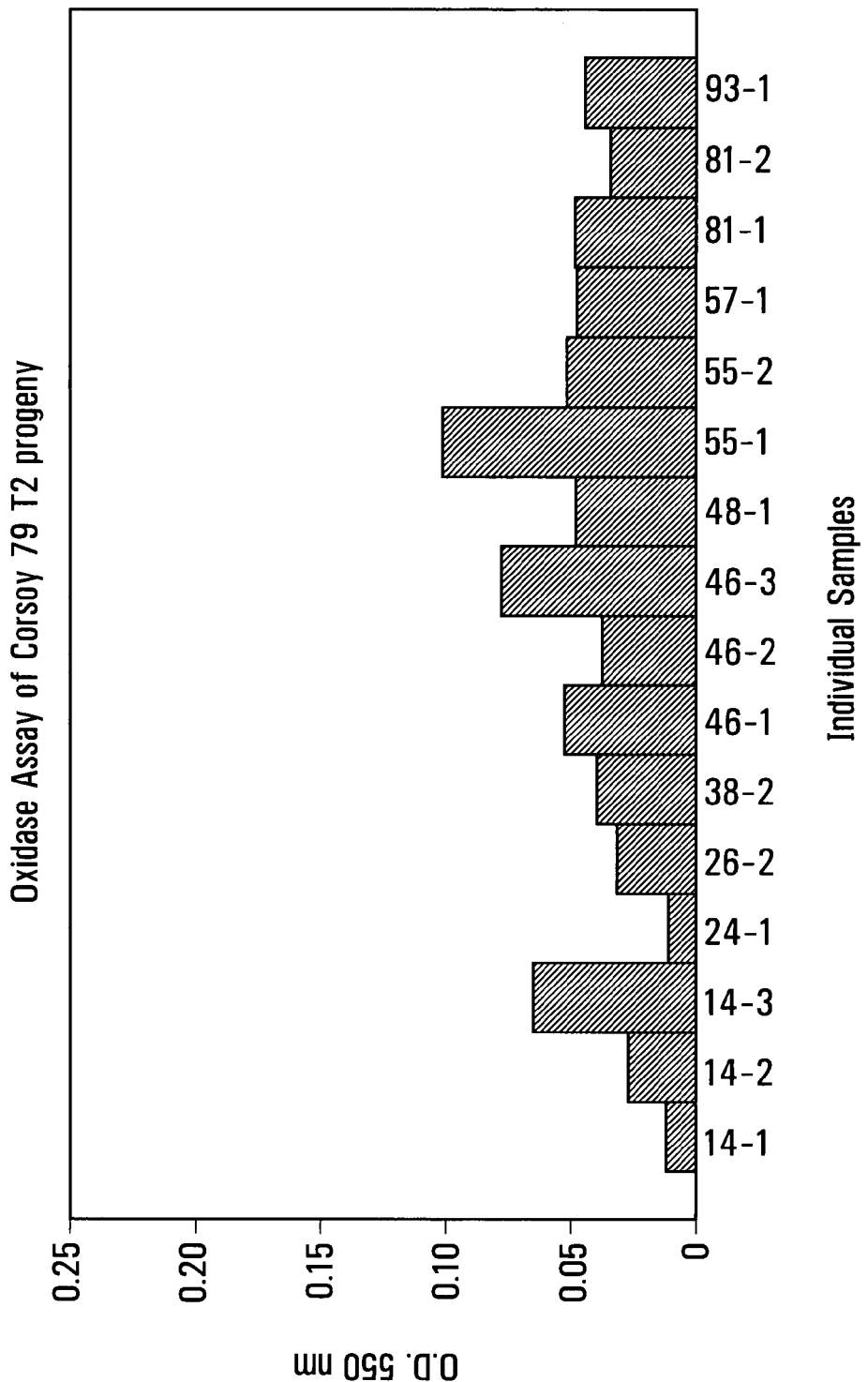
FIG. 5 is a graph representing OAO activity in the $T_2$ progeny of the originally transformed Corsoy 79 soybean seedlings.
Figure 6:
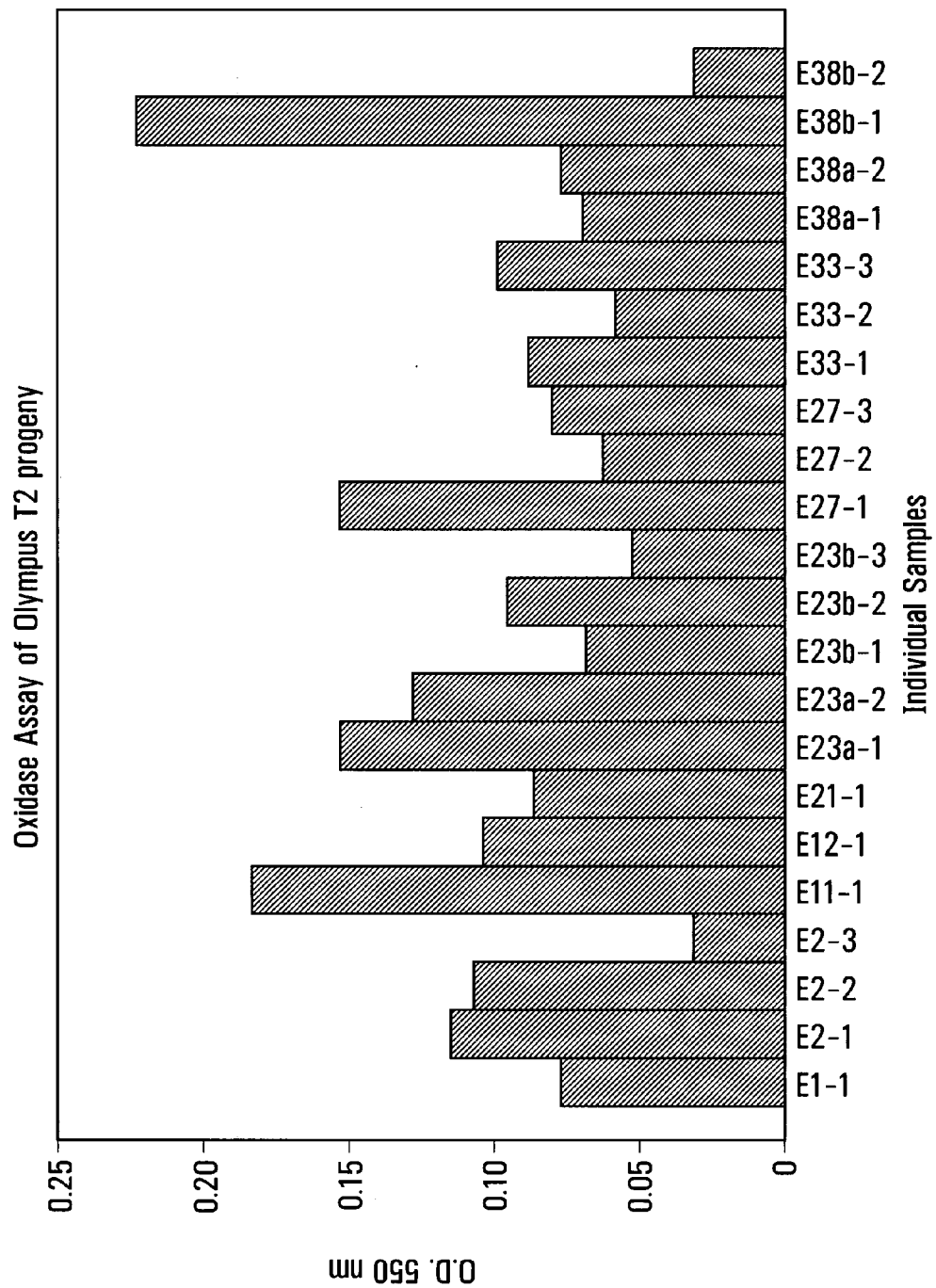
FIG. 6 is a graph representing OAO activity in the $T_2$ progeny of the originally transformed Olympus soybean seedlings.

The $T_2$ generation of initially transformed Corsoy 79 and Olympus plants were analyzed for the presence of barley OAO by assaying for OAO activity. This colorimetric assay reveals the OAO activity by monitoring the production of hydrogen peroxide which reacts with the N-N dimethylahiline substrate to provide a colored compound. Absorbance at 550 nm is proportional to the amount of hydrogen peroxide produced by OAO. Background levels of hydrogen peroxide production in untransformed leaf tissue determined in triplicate were subtracted from the results. The data in FIGS. 5 and 6 show a significant amount of oxidase activity present in the $T_2$ generations of Olympus and Corsoy 79 soybean transformants, respectively, as compared to untransformed plants. Therefore, transformation of seedlings using the methods of the present invention produced transformed plants with characteristics that are inherited.

Figure 7:
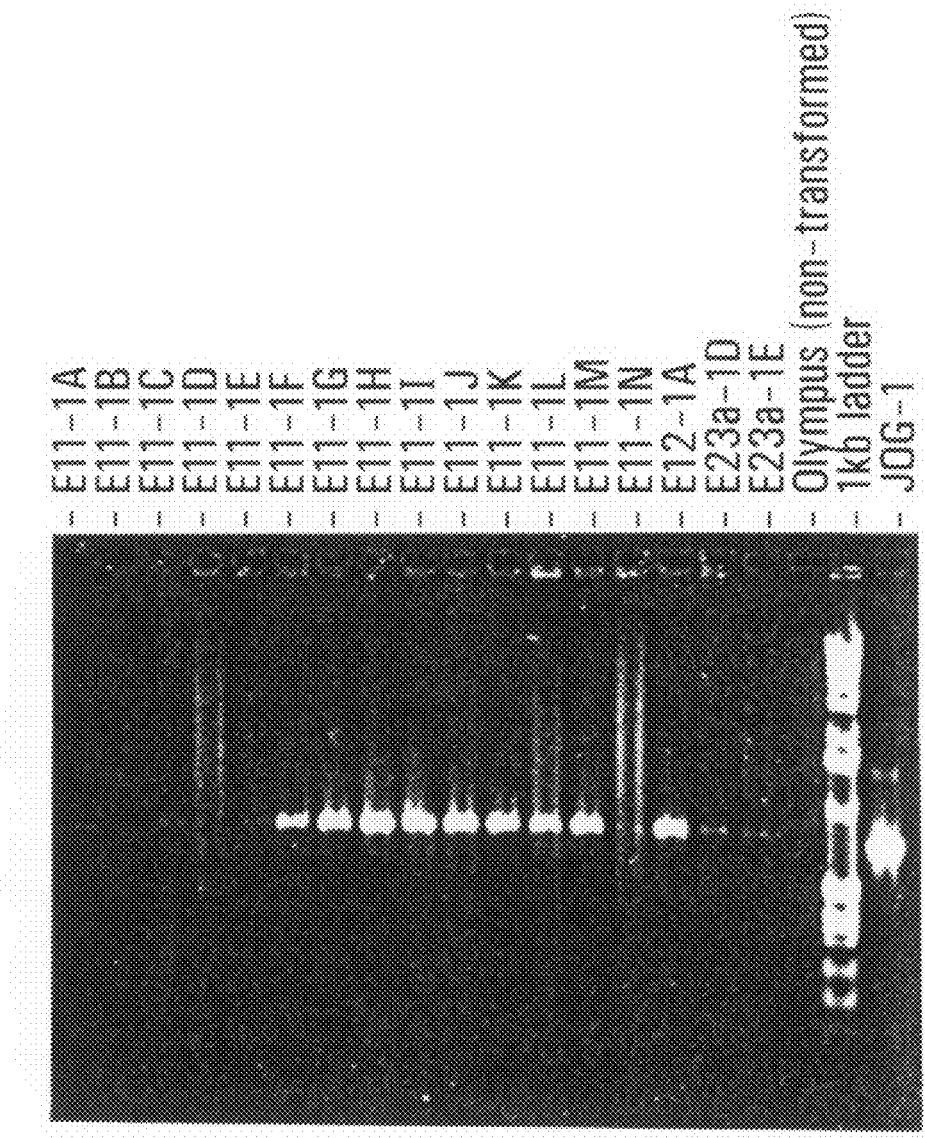
FIG. 7 is a photograph of an agarose gel showing the PCR amplification of the NptII transgene in $T_3$ progeny of the originally transformed Olympus soybean seedlings.

The production of transgenic progeny from seedlings transformed by the methods of the present invention was also shown by analysis of the $T_3$ generation of originally transformed Olympus soybeans. PCR amplification of the reporter gene, nptII, from $T_3$ generation plants showed the presence of the reporter gene in 8 out of 14 plants (FIG. 7, E11-1A through E11-1N). The reporter gene was not present in the $T_3$ generation of non-transformed Olympus soybean.

This Specific Example illustrates the efficiency, ease and effectiveness of the methods of the present invention in introducing DNA into plants. Roughly 10% of the seedlings which withstood the transformation process described herein yielded progeny that were transformed. The transgene is therefore integrated in such a way that it is passed to progeny in a Mendelian fashion.

The foregoing discussion discloses and describes merely exemplary embodiments of the present invention. One skilled in the art will readily recognize from such discussion, and from the accompanying drawing and claims, that various changes, modifications and variations can be made therein without departing from the spirit and scope of the invention as defined in the following claims.

All references cited herein, including literature references and patents, are incorporated by reference as if fully set forth.

We claim:

1. A method for transforming a seedling of soybean or dry bean comprising the steps of:
    (a) contacting the apical meristem of the soybean or dry bean seedling with a medium comprising DNA;
    (b) suspending the root of the soybean or dry bean seedling in buffer and contacting said root with a positive lead of a power source;
    (c) contacting the medium comprising DNA in step (a) with a negative lead of the power source; and
    (d) applying a low amperage current from the power source, thereby causing the DNA to migrate from the medium to the cells of the apical meristem of the soybean or dry bean seedling.

2. The method of claim 1, wherein the DNA is a plasmid vector.

3. The method of claim 2, wherein the plasmid vector is linearized.

4. The method of claim 2, wherein the plasmid vector contains a gene for barley oxalic acid oxidase.

5. The method of claim 1, wherein the current is about 0.01 to about 1.0 mA.

6. The method of claim 1, wherein the current is about 0.1 to about 0.5 mA.

7. A method for producing seed of a transformed soybean or dry bean plant comprising the steps of:
  (a) growing a transformed soybean or dry bean plant from the transformed seedling produced by the method of claim 1;
  (b) propagating the transformed soybean or dry bean plant;
  (c) pollinating the transformed soybean or dry bean plant; and
  (d) harvesting seed from the transformed soybean or dry bean plant.

8. A method for transforming a seedling of soybean or dry bean comprising the steps of:
  (a) contacting the apical meristem of the soybean or dry bean seedling with a medium comprising DNA, wherein said DNA comprises a plasmid vector having a T-DNA region and border sequences;
  (b) suspending the root of the soybean or dry bean seedling in buffer and contacting said root with a positive lead of a power source;
  (c) contacting the medium comprising DNA in step (a) with a negative lead of the power source; and
  (d) applying a low amperage current from the power source, thereby causing the DNA to migrate from the medium to the cells of the apical meristem of the soybean or dry bean seedling.

9. The method of claim 8 wherein the plasmid vector contains a gene for barley oxalic acid oxidase.

10. The method of claim 8, wherein the plasmid vector is linearized.

11. The method of claim 8, wherein the current is about 0.01 to about 1.0 mA.

12. The method of claim 8, wherein the current is about 0.1 to about 0.5 mA.

* * * * *